July 11, 1972 W. A. WARRINER Plant Pat. 3,235
ROSE PLANT
Filed Jan. 7, 1971
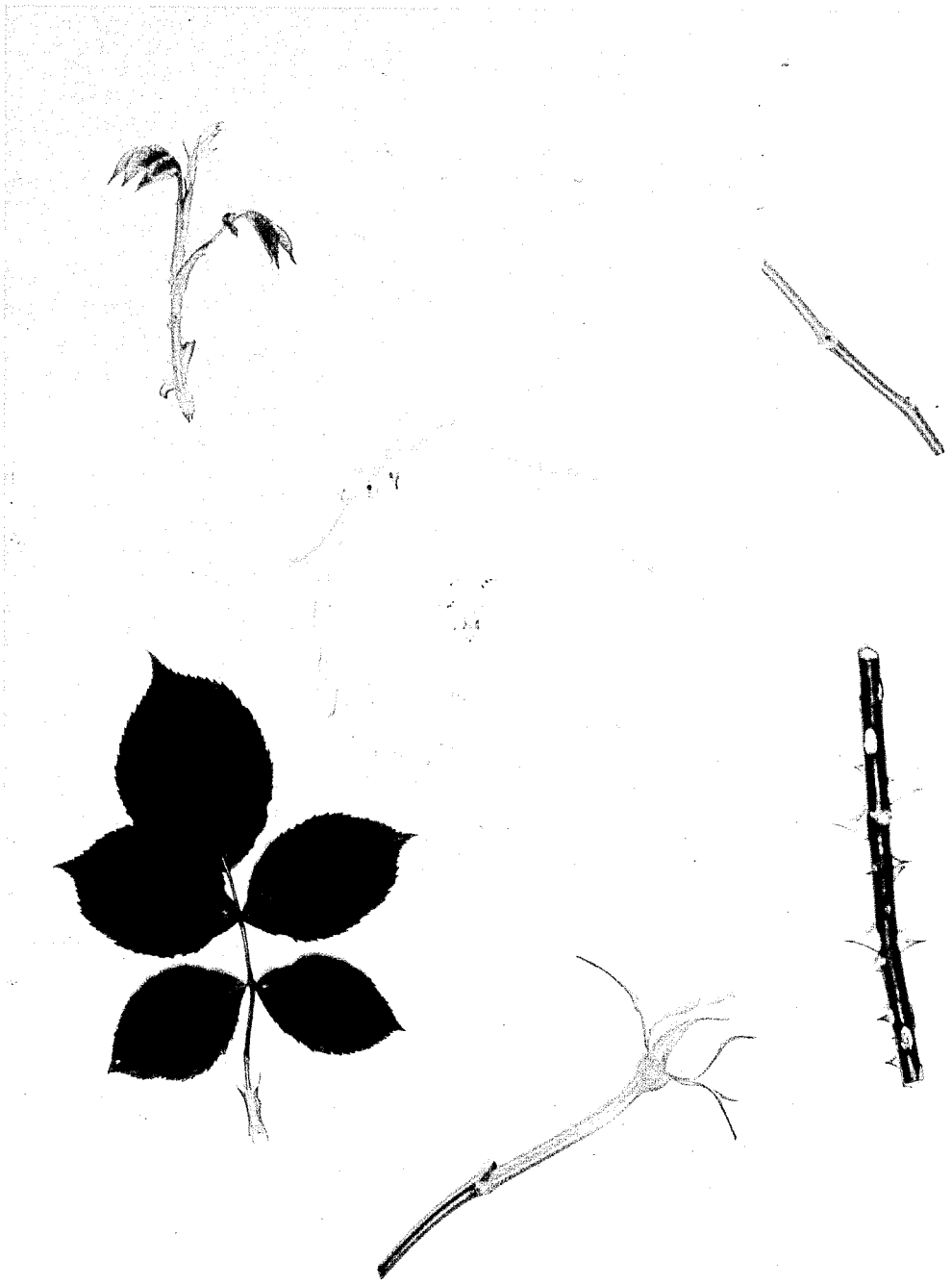
WILLIAM A. WARRINER
INVENTOR
BY
BUCKHORN BLORE KLARQUIST & SPARKMAN
ATTORNEYS

United States Patent Office

Plant Pat. 3,235
Patented July 11, 1972

3,235
ROSE PLANT

William A. Warriner, Tustin, Calif., assignor to Jackson & Perkins Company, Medford, Oreg.

Filed Jan. 7, 1971, Ser. No. 104,820
Int. Cl. A01h 5/00
U.S. Cl. Plt.—23 1 Claim The present invention relates to a new and distinct variety of rose plant of the floribunda class discovered by me as a mutation of the variety Bridal Pink, U.S. Plant Pat. No. 2,851.

One branch of a Bridal Pink plant growing in a cultivated row of Bridal Pink plants at Livermore, Calif. in 1965 was discovered by me to produce nearly white flowers as compared to the normally light pink flowers of Bridal Pink.

Repeated testing of this new mutation showed that the variety was very similar to Bridal Pink in plant habit, growth patterns and flower form, but distinctly different from Bridal Pink and any other variety of which I am aware in flower color. The bud color of the new variety is lighter than Barium Yellow of Wilson's "Horticultural Color Chart." The open flower is nearly white with a very light overlay of light pink, especially evident in the center of the flower.

Asexual reproduction of my new variety by budding as performed at Wasco, Calif. shows that the aforementioned characteristics and distinctions propagate true to form and are established and transmitted through succeeding propagations.

The accompanying drawing shows typical specimens of the vegetative growth and flowers of this new variety in different stages of development, depicted in color as nearly true as it is reasonably possible to make the same in a color illustration of this character.

The following is a detailed description of my new variety with color terminology from Wilson's "Horticultural Color Chart," except where ordinary dictionary significance of color is indicated.

Parentage: Sport.
*Parent variety.*—Bridal Pink, Plant Pat. No. 2,851.
Classification:
*Botanic.*—*Rosa hybrid.*
*Commercial.*—Floribunda.

*Flower*

(Observations made at Irvine, Calif. in morning during November of greenhouse flowers.)

Blooming habit: Recurrent—continuous.
Bud:
*Size.*—Medium.
*Form.*—Pointed, ovoid.
*Color.*—When sepals first divide—slightly lighter than Barium Yellow (503/3) with a very light overlay around the petal edges of Dawn Pink (523/2). When half blown—inside of petals, outer petals are Uranium Green (63/3) to near white; inner petals are Uranium Green to near white with faint pink (unidentifiable by the chart) overcast when viewed from tip to base; pink is not visible when viewed from base to tip; reverse of petals—nearly white.
*Sepals.*—Color: Inside: Pod Green (061/2) overlaid with Lettuce Green (861/1); near outer edges—slightly tomentose; outside—Pod Green (061) at midrib area, overlaid with Lettuce Green (861) near outer edges. Three appendaged sepals lightly appendaged. Two unappendaged sepals smooth edged.
*Receptacle.*—Color: Lettuce Green (861). Shape: funnel. Size: long. Surface: smooth.
*Peduncle.*—Length: Medium. Surface: very slightly prickly. Color: Lettuce Green (861/1). Strength: stiff, erect.
*Opening.*—Petals curl back slowly.
Bloom:
*Size.*—Large (3½"–4").
*Borne.*—Singly and several together.
*Stems.*—Long.
*Form.*—When first open—high centered. Permanence—retains its form to the end.
*Petalage.*—From 30–35 petals.
*Color.*—Center of flower: Upper side of petals near white with faint overlay of pink—near Dawn Pink (523/3) but too faint to positively identify. Reverse side of petals—same as upper side. Outer petals: Upper side of petals—near white—no pink overlay. Reverse of petals—near white—no pink overlay. Base of petals—small area of Primrose Yellow (601/2). General tonality from distance—near white (Pale Ivory) with very slight pink overcast, especially when viewed from above. No variegations.
*Discoloration.*—General tonality at end of first day—remains the same as just open color. Third day—remains the same as just open color.
*Fragrance.*—None.
Petals:
*Texture.*—Thick, leathery.
*Surface.*—Inside—satiny. Reverse—satiny.
*Shape.*—Near round.
*Form.*—Tips slightly recurved.
*Arrangement.*—Imbricated.
*Petaloids in center.*—Few.
*Persistence.*—Drop off cleanly.
*Lastingness.*—On the plant—long. As cut flower—long.
Reproductive parts:
*Stamens, anthers.*—Medium, many; regularly arranged around styles. Color—yellow.
*Stamens, filaments (threads).*—Medium and short. Color—yellow.
*Pollen.*—Color—lemon yellow.
*Styles.*—Loosely separated, of uneven length. Color—red.
*Stigmas.*—Color—white.
*Ovaries.*—All enclosed in calyx.

*Plant*

Form: Bush.
Growth: Vigorous.
Foliage: Compound of 5 or 7 leaflets.
*Size.*—Large.
*Quantity.*—Abundant.
*Color.*—New foliage: Lettuce Green (861/3), heavily overlaid as leaves unfold with large areas of Garnet Brown (00918/3). Old foliage: Upper side—slightly darker than Parsley Green (00962); lower side—near Lavender Green (00761).
*Leaflets.* — Shape—elliptic. Texture—upper side—leathery; under side—smooth; ribs and veins—ordinary. Edge—serrated, undulated. Serration—single; small. Petiole—rachis—color—green lower edge; reddish upper edge; underside—prickles. Stipules—long and narrow. Smooth. Disease resistance—very resistant to mildew under normal growing conditions at Irvine and Wasco, California.

Wood:

*New wood.*—Color—Spinach Green (0960/3). Bark—smooth.

*Old wood.*—Color—same as new wood. Bark—smooth.

Thorns:

*Quantity.*—On main stalks from base—ordinary. On laterals from stalk—ordinary.

*Form.*—Narrow base; long; slightly hooked downward.

*Color (when young).*—Garnet Brown (00918).

*Position.*—Irregular.

*Prickles.*—Quantity: On main stalks—few; on laterals—few. Color: Brown.

*Short needles.*—Quantity: on main stalks—none; on laterals—none.

I claim:

1. A new and distinct variety of rose plant of the floribunda class, substantially as herein shown and described, characterized particularly as to novelty by the unique combination of its similarity to Bridal Pink in plant habit and growth and its novel color of near white with a very faint pink overcast.

No references cited.

ROBERT E. BAGWILL, Primary Examiner